United States Patent
Cheng et al.

[11] Patent Number: 6,043,241
[45] Date of Patent: Mar. 28, 2000

[54] KETOACID ENDOTHELIN ANTAGONISTS

[75] Inventors: Xue-Min Cheng, Ann Arbor, Mich.; Annette Marian Doherty, Paris, France; Timothy Robert Hurley; Michael James Lovdahl, both of Ann Arbor, Mich.; William Chester Patt, Chelsea, Mich.; Joseph Thomas Repine, Ann Arbor, Mich.

[73] Assignee: Warner-Lambert Company, Morris Plains, N.J.

[21] Appl. No.: 09/117,575

[22] PCT Filed: Mar. 12, 1997

[86] PCT No.: PCT/US97/03959

§ 371 Date: Jul. 31, 1998

§ 102(e) Date: Jul. 31, 1998

[87] PCT Pub. No.: WO97/37987

PCT Pub. Date: Oct. 16, 1997

Related U.S. Application Data

[60] Provisional application No. 60/015,269, Apr. 10, 1996.

[51] Int. Cl.⁷ .......................... A61K 31/36; C07D 317/54
[52] U.S. Cl. ....................... 514/233.8; 514/452; 544/148; 549/438; 549/447; 562/463
[58] Field of Search ..................................... 549/438, 447; 562/463

[56] References Cited

U.S. PATENT DOCUMENTS 5,559,105  9/1996  Bryan et al. ............................... 514/63
5,691,373  11/1997  Berryman et al. .................. 549/438 X

*Primary Examiner*—Fiona T. Powers
*Attorney, Agent, or Firm*—Elizabeth M. Anderson

[57] ABSTRACT

Compounds of the Formula I

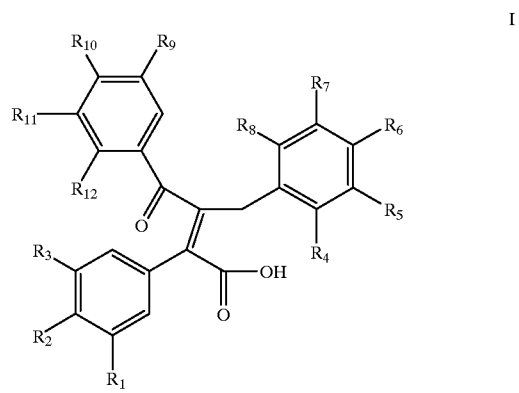

are nonpeptide antagonists of endothelin which are useful in treating a variety of diseasses such as elevated levels of endothelin, acute respiratory distress syndrome (ARDS), atherosclerosis, restenosis, Raynaud's phenomenon etc. The compounds are prepared by reacting an alpha-hydroxy butenolide with one or more equivalents of a suitable base, and exposing the solution to UV light.

32 Claims, No Drawings

KETOACID ENDOTHELIN ANTAGONISTS

This application claims priority from copending provisional application Ser. No. 60/015,269 filed Apr. 10, 1996.

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, acute respiratory distress syndrome (ARDS), angina, arrhythmias, asthma, atherosclerosis, benign prostatic hyperplasia, Buerger's Disease, cardiac arrest, cardiogenic shock, cerebral trauma, Chrohn's Disease, cryptogenic fibrosing alveolitis, chronic obstructive pulmonary diseases, congenital heart disease, congestive heart failure (CHF) (mild), congestive heart failure (CHF) (severe), cerebral ischemia, cerebral infarction, cerebral vasospasm, cirrhosis, diabetes, dilated cardiomyopathy, drowning (anoxia), endotoxic shock, gastric mucosal damage, glaucoma, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, male penile erectile dysfunction, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasu's arteritis, ulcerative colitis, uremia after hemodialysis, and uremia before hemodialysis.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include: ET-2, ET-3, vasoactive intestinal contractor (VIC), and the sarafotoxins (SRTXs).

The distribution of the two cloned receptor subtypes, termed $ET_A$ and $ET_B$, have been studied extensively (Arai H., et al., Nature, 1990;348:730, Sakurai T., et al., Nature, 1990;348:732). The $ET_A$, or vascular smooth muscle receptor, is widely distributed in cardiovascular tissues and in certain regions of the brain (Lin H. Y., et al., Proc. Natl. Acad. Sci., 1991;88:3185). The $ET_B$ receptor, originally cloned from rat lung, has been found in rat cerebellum and in endothelial cells. The human ET receptor subtypes have been cloned and expressed (Sakamoto A., et al., Biochem. Biophys. Res. Chem., 1991;178:656, Hosoda K., et al., FEBS Lett., 1991;287:23). The $ET_A$ receptor clearly mediates vasoconstriction and there have been a few reports implicating the $ET_B$ receptor in the initial vasodilatory response to ET (Takayanagi R., et al., FEBS Lett., 1991;282:103). However, recent data has shown that the $ET_B$ receptor can also mediate vasoconstriction in some tissue beds (Panek R. L., et al., Biochem. Biophys. Res. Commun., 1992;183(2):566).

The involvement of endothelin has been proven in many human disease states.

Elevated levels of endothelin have been measured in patients suffering from ischemic heart disease (Yasuda M., et al., Amer. Heart J., 1990;119:801–806) and either stable or unstable angina (Stewart J. T., et al., Br. Heart J., 1991;66:7–9).

The degree of elevation of plasma ET levels in patients with heart failure varies from 2-fold to 5-fold (Stewart, et al., Circulation, 1992;85:510–517; Lerman, et al., J. Am. Coll. Cardiology, 1992;20:849–853). The greatest elevation measured appears to be in congestive heart failure (CHF) patients with marked pulmonary hypertension. The increased level of circulating ET in human congestive heart failure patients also correlated with the severity of the disease observed (Rodeheffer, et al., Am. J. Hypertension, 1991:4:9A; Rodeheffer, et al., Mayo Clin. Prod., 1992;67:719–724).

Many studies have indicated increased plasma levels of ET-1 after acute myocardial infarction (MI) in both animals and humans (Stewart, et al., J. Am. Coll. Cardiol., 1991:18:38–43; Tomoda, et al., Am. Heart J., 1993;125:667–672; Ray, et al., Br. Heart J., 1992;67:383–386; Tsuji, et al., Life Sci., 1991;48:1745–1749). It has also been reported that the action of ET-1 may be enhanced under the conditions of ischemia (Liu, et al., Biochem. Biophys. Res. Commun., 1989;164:1220–1225).

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of the infarction in a dose-dependent manner (Watanabe T., et al., "Endothelin in Myocardial Infarction," Nature, (Lond.) 1990;344:114). Thus, ET may be involved in the pathogenesis of congestive heart failure and myocardial ischemia (Margulies K. B., et al., "Increased Endothelin in Experimental Heart Failure," Circulation, 1990;82:2226).

Patients with chronic heart failure were treated with the ET antagonist Bosentan, which was found to improve cardiac performance, concluding that ET is involved in the regulation of vascular tone and that inhibition of its effects may be beneficial in chronic heart failure (Kiowski W., et al., Lancet, 1995;346:732–36, also J. Am. Coll. Cardiol., 1995; special edition 296A:779–1).

Infusion of an endothelin antibody 1 hour prior to and 1 hour after a 60 minute period of renal ischaemia resulted in changes in renal function versus control. In addition, an increase in glomerular platelet-activating factor was attributed to endothelin (Lopez-Farre A., et al., J. Physiology, 1991;444: 513–522). In patients with chronic renal failure as well as in patients on regular hemodialysis treatment mean plasma endothelin levels were significantly increased (Stockenhuber F., et al., Clin. Sci. (Lond.), 1992;82:255–258).

Studies by Kon and colleagues using anti-ET antibodies in an ischemic kidney model, to deactivate endogenous ET, indicated the peptide's involvement in acute renal ischemic injury (Kon V., et al., "Glomerular Actions of Endothelin In Vivo," J. Clin. Invest., 1989;83:1762).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno A., Effects of Endothelin-Specific Antibodies and Endothelin in Spontaneously Hypertensive Rats," J. Tokyo Women's Med. Coll., 1991;61:951).

Other studies have demonstrated the usefulness of ET antagonists in maintaining beneficial parameters of renal performance following ischemia-induced injuries (Mino, et al., *Eur. J. Pharmacol.*, 1992;221:77–83; Benigni, et al., *Kidney Int.*, 1993;44:440–444).

$ET_A$ receptor mRNA has been detected in 82% of human meningiomas (*J. Clin. Invest.*, 1995;66:2017–2025

Plasma endothelin-1 levels were dramatically increased in a cancer patient with malignant hemangioendothelioma (Nakagawa K., et al., *Nippon Hifuka Gakkai Zasshi*, 1990;100:1453–1456).

Exogenous endothelin-1 is also a prostate cancer mitrogen in vitro. Endothelin levels are significantly elevated in men with metastatic prostate cancer. Every human prostate cancer cell line tested by Nelson et al., (*Nature Medicine*, 1995; Vol 1(9):944) produced ET-1 mRNA and secreted immunoreactive endothelin.

An ET antagonist, PD 155080 was found to mediate prostate smooth muscle function in vivo, which demonstrated that endothelin antagonists may be useful in the treatment of benign prostatic hyperplasia (Chleko I., et al., Annual Meeting of the American Urological Assn, Orlando, 1996).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Respir. Dis.*, 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B. A., et al., *Am. J. Obstet. Gynecol.*, 1992;166:962–968).

Plasma immunoreactive endothelin-1 concentrations are elevated in patients with sepsis and correlate with the degree of illness and depression of cardiac output (Pittett J., et al., *Ann. Surg.*, 1991;213(3):262).

In addition, the ET-1 antagonist BQ-123 has been evaluated in a mouse model of endotoxic shock. This ETA antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry*, 1990;265(29):17432). In addition increased levels of plasma ET-1 have been observed in microalbuminuric insulin-dependent diabetes mellitus patients indicating a role for ET in endocrine disorders such as diabetes (Collier A., et al., *Diabetes Care*, 1992;15(8):1038).

Infusion of ET-1 produced a sustained, reversible, and salt-dependent hypertension when infused into normal, conscious rats (Mortensen, et al., *Hypertension*, 1990;15:720–723; Mortensen, et al., *FASEB J.*, 1991;5:A1105).

$ET_A$ antagonist receptor blockade has been found to produce an antihypertensive effect in normal to low renin models of hypertension with a time course similar to the inhibition of ET-1 pressor responses (Basil M. K., et al., *J. Hypertension*, 1992;10(Suppl. 4):S49). The endothelins have been shown to be arrhythmogenic, and to have positive chronotropic and inotropic effects, thus ET receptor blockade would be expected to be useful in arrhythmia and other cardiovascular disorders (Han S.-P., et al., *Life Sci.*, 1990;46:767).

Recently, an $ET_A$ selective antagonist demonstrated an oral antihypertensive effect (Stein P. D., et al., "The Discovery of Sulfonamide Endothelin Antagonists and the Development of the Orally Active $ET_A$ Antagonist 5-(Dimethylamino)-N-(3,4-dimethyl-5-isoxazolyl)-1-naphthalenesulfonamide," *J. Med. Chem.*, 1994;37: 329–331.

Plasma ET levels are elevated in patients with pulmonary hypertension (Yoshibayashi M., et al., *Circulation*, 1991;84:2280–2285). Increased expression has been measured indicating local production in the lung. Pulmonary hypertension is associated with the increased expression of endothelin-1 in vascular endothelial cells, suggesting that the local production of endothelin-1 may contribute to vascular abnormalities associated with pulmonary hypertension (Giaid A., et al., *N. Enal. J. Med.*, 1993;328:1732–9). In pulmonary hypertension, ET-1 is the most potent constrictor of airway smooth muscle thus far described in vitro (Pons, et al.,*J. Pharmacol.*, 1991;102: 791–796). This response has been blocked by $ET_A$-receptor antagonists (Abraham, et al., *J. Appl. Physiol.*, 1993;74(5);2537–2542). Endothelin antagonists that block the production of endothelin and hence lower levels of endothelin have shown efficacy in several animal models of pulmonary hypertension. Pulmonary hypoxia increases ET-1 expression in the lung (*J. Surg. Res.*, 1994;57:280–283). For example, BQ-123, Bosentan, and PD 156707 provide protection in a rat hypoxia model of hypertension by lowering the increase in pulmonary vascular resistance and pulmonary arterial pressure (Eddahibi S., et al., *Am. J. Physiol.*, 1995;268:H828–835; Bonvallet S. T., et al., *Am. Rev. Resp. Dis.*, 1993;147:A493; IBC International Conference, R. Bialecki, Feb. 5, 1996, Coronado, Calif.). $ET_A$-receptor antagonists have been found to prevent and reverse chronic hypoxia-induced pulmonary hypertension in rat (DiCarlo, et al., *Am. J. Physiol.*, 1995;269:L690–L697; Chen, et al., *J. Appl. Physiol.*, 1995;79(6):2122–2131).

There is evidence that suggests the extent of increase in plasma ET-1 levels in patients with pulmonary hypertension may reflect the abnormalities of pulmonary circulation. It has been demonstrated that the pulmonary artery endothelial cells are injured in patients with congenital heart disease (Ishikawa S., et al., *J. Thorac. Cardiovasc. Surg.*, 1995;110:271–3). Further, in cardiopulmonary bypass operations on patients with congenital heart disease, an immediate postoperative increase in circulating endothelin was observed which may predispose the patient to pulmonary vascular lability and crises in the postoperative period (Komai H., et al., *J. Thorac. Cardiovasc. Surg.*, 1993;106:473–8).

The widespread localization of the endothelins and their receptors in the central nervous system and cerebrovascular circulation has been described (Nikolov R. K., et al., *Drugs of Today*, 1992;28(5):303–310). Intracerebroventricular administration of ET-1 in rats has been shown to evoke several behavioral effects. The potent vasoconstrictor action of ETs on isolated cerebral arterioles suggests the importance of these peptides in the regulation of cerebrovascular tone. These factors strongly suggest a role for the ETs in neurological disorders.

The volume of ischemic damage in the cerebral hemisphere of cats following middle cerebral artery occlusion was significantly reduced after the IV administration of PD 156707 (Patel, et al., *J. Cardiovasc. Pharmacol.*, 1995;26 (Suppl. 3):S412–S415). Reduction of ischemic brain injury in rats was also demonstrated following oral administration of the endothelin antagonist SE 217242 (Barone, et al., *J. Cardiovasc. Pharmacol.*, 1995;26(Suppl. 3): S404–S407).

Several studies have shown that endothelin levels are elevated in acute and chronic renal failure (Torralbo A., et al., *Am. J. Kid. Dis.*, 1995;25(16):918–923). Data in models of acute renal failure indicate that endothelin plays an important role. An endothelin receptor antagonist Bosentan that can block endothelin production and thereby lower levels has been reported to be effective in models of acute renal ischemia (Clozel M., et al., *Nature*, 1995;365:759). In dogs, the endothelin receptor antagonist SB 2090670 can attenuate ischemia-induced reductions in glomerular filtration rate and increases in fractional sodium excretion (Brooks D. P., et al., *J. Pharmacol. Exp. Ther.*, 1995). In addition, several antagonists have been shown to block radiocontrast-induced nephrotoxicity (Oldroyd S., et al., *Radiology*, 1995;196:661–665).

TAK-044 has shown protective effects in a model of acute renal failure in rats (*Life Sci.*, 1994;55(4): 301–310).

The $ET_A$ antagonist BQ-123 has been shown to prevent early cerebral vasospasm following subarachnoid hemorrhage (SAH) (Clozel M. and Watanabe H., *Life Sci.*, 1993;52:825–834; Lee K. S., et al., *Cerebral Vasospasm*, 1993:217; and *Neurosurgery*, 1994;34:108). FR 139317 significantly inhibited the vasoconstriction of the basilar artery after 7 days in a canine two-hemorrhage model of SAH (Nirei H., et al., *Life Sci.*, 1993;52:1869). BQ-485 also significantly inhibited the vasoconstriction of the basilar artery after 7 days in a canine two-hemorrhage model of SAH (Yano, et al., *Biochem. Biophys. Res. Commun.*, 1993; 195:969). Ro 46-2005 (Clozel M., et al., *Nature*, 1993;365:759) has been shown to prevent early cerebral vasospasm following SAH in the rat with no significant effect on systemic arterial blood pressure. Treatment with Ro 47-0203=Bosentan (Clozel, et al., *Circulation*, 1993;88(4) part 2:0907) to rabbits with SAH had a 36±7% reduction of basilar artery cross-sectional area compared to sham rabbits. All of these studies show in vivo efficacy of endothelin antagonists in cerebral vasospasm resulting from SAH.

Circulating and tissue endothelin immunoreactivity is increased more than 2-fold in patients with advanced atherosclerosis (Lerman A., et al., *New England J. Med.*, 1991;325:997–1001). Increased endothelin immunoreactivity has also been associated with Buerger's disease (Kanno K., et al., *J. Amer. Med. Assoc.*, 1990;264:2868) and Raynaud's phenomenon (Zamora M. R., et al., *Lancet*, 1990;336:1144–1147).

An increase of circulating endothelin levels was observed in patients that underwent percutaneous transluminal coronary angioplasty (*PTCA*) (Tahara A., et al., *Metab. Clin. Exp.*, 1991;40:1235–1237.

In an experiment to minimize restenosis following carotid artery balloon angioplasty in rats, the ET receptor antagonist SB 209670 was found to ameliorate neointima formation (Douglas, et al., *Circulation Res.*, 1994;75:190–197).

Local intra-arterial administration of endothelin has been shown to induce small intestinal mucosal damage in rats in a dose-dependent manner (Mirua S., et al., *Digestion*, 1991;48:163–172; Masuda E., et al., *Am. J. Physiol.*, 1992;262:G785–G790). Elevated endothelin levels have been observed in patients suffering from Crohn's disease and ulcerative colitis (Murch S. H., et al., *Lancet*, 1992;339:381–384).

The ET receptor antagonist bosentan was found to be an antagonist toward the ET-1-induced changes in gastric mucosal hemodynamics as well as on ET-1-induced gastric ulceration (Lazaratos, et al., *Pharmacol. Lett.*, 1995;56(9):195–200).

Graefe's *Arch. Clin. Exp. Ophthalmol*, 1995;233(8):484–488 provides data to support the hypothesis that vascular dysfunction may be involved in the pathogenesis of optic nerve damage in normal-tension glaucoma.

*Eur. J. Pharmacol.*, 1996;307(1):69–74 teaches a role for endothelins in penile erection.

Release of eicosanoids and endothelin in an experimental model of adult respiratory distress syndrome (ARDS) is covered in *Agents Actions Suppl., Prostaglandins Cardiovasc. Syst.*, 1992;37:41–6.

*Am. Rev. Respir. Dis.*, 1993;148:1169–1173 teaches venous ET-1 concentrations are massively increased in ARDS as a result of both increased formation and decreased clearance.

*Chest*, 1993;104:476–80 shows plasma ET-1 levels also positively correlate with right atrial pressure, systolic pulmonary arterial pressure, mean pulmonary arterial pressure, and resistance ratio (pulmonary vascular resistance/systemic vascular resistance) in ARDS.

In chronic obstructive pulmonary disease (COPD) and Cor Pulmonale associated with pulmonary hypertension patients excrete higher amounts of ET-1 compared to healthy subjects. Urinary ET-1 levels are further increased during acute exacerbation of the disease.

ET-1 levels in broncho alveolar lavage fluid from patients with COPD have been reported. ET-1 is involved in pulmonary endothelium damage caused by hypoxia in COPD patients. Pulmonary artery hypertension is the primary cardiovascular complication in COPD. (See Sofia, et al., *Respiration*, 1994:263–268(61); "Increased 24-Hour endothelin-1 urinary excretion in patients with chronic obstructive pulmonary disease" and Matthay, et al., *Medical Clinics of North America*, 1990:571–618(74); "Cardiovascular pulmonary interaction in chronic obstructive pulmonary disease with special reference to the pathogenesis and management of Cor Pulmonale."

ET-1 expression is increased in the lung vasculature of patients with pulmonary hypertension contributes to the medial hyperplasia and intimal fibrosis of cryptogenic fibrosing alveolitis. See Giaid, et al., *The Lancet*, 1993:1550–1554(341) Expression of endothelin-1 in lungs of patients with cryptogenic fibrosing alveolitis.

In summary, some of the conditions in which ET antagonists may be useful in treatment are as follows: acute respiratory distress syndrome (ARDS), angina, arrhythmias, asthma, atherosclerosis, benign prostatic hyperplasia, Buerger's Disease, cardiac arrest, cardiogenic shock, cerebral trauma, Chrohn's Disease, congenital heart disease, congestive heart failure (CHF) (mild), congestive heart failure (CHF) (severe), cerebral ischemia, cerebral infarction, cerebral vasospasm, chronic obstructive pulmonary diseases, cirrhosis, diabetes, dilated cardiomyopathy, drowning (anoxia), endotoxic shock, gastric mucosal damage, glaucoma, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, male penile erectile dysfunction, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasu's arteritis, ulcerative colitis, uremia after hemodialysis, and uremia before hemodialysis.

WO 97/01173 relates to a process for the production of aromatic olefins of the formula $$Ar(R_1)C=C(R_2)R_3$$

wherein

Ar is a radical selected from the group consisting of unsubstituted carbocyclic and heterocyclic aryl and carbocyclic and heterocyclic aryl substituted by one or more radicals selected from the group consisting of alkyl, carbocyclic aryl or aralkyl, fluoro, chloro, cyano, nitro, $OR_4$, S-alkyl, $COR_4$, $CO_2R_4$, and $SO_3R_4$, wherein $R_4$ is hydrogen, alkyl, carbocyclic aryl or aralkyl; and $R_1$, $R_2$, and $R_3$ are the same or different and each represent hydrogen, alkyl, carbocyclic aryl or aralkyl, chloro, fluoro, cyano, nitro, $OR_5$, $CO_2R_5$, $COR_5$, and —$(R_2)C=C(R_2)R_3$, wherein $R_5$ is hydrogen, alkyl, carbocyclic aryl or aralkyl, which comprises catalytic vinylation of an aryl chloride of the formula ArCl with an olefinic compound of the formula $H(R_1)C=C(R_2)R_3$, wherein Ar, $R_1$, $R_2$, and $R_3$ are as defined above, in the presence of a base and of a palladium complex catalyst of the formula $$[R_6R_7P(CH_2)_nPR_8R_9]_2Pd$$

wherein n is 3 or 4, and $R_6$ to $R_9$ are selected from hydrogen, alkyl, cycloalkyl, unsubstituted carbocyclic aryl or aralkyl, and carbocyclic aryl or aralkyl substituted by alkyl, alkoxy, or phenoxy.

Japanese application 3258744A discloses production of unsaturated carbonyl compounds (I) comprising reacting an organosilicon compound (II) with an unsaturated compound (III) in an ether solvent in the presence of a group VIII transition metal catalyst, carbon monoxide, and fluoride ions $$R_1SiR_2R_3R_4 \quad (II)$$

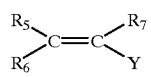
(III)

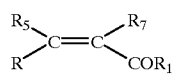
(I)

$R_1$=opt. substd. alkyl, alkenyl, aryl, or alkynyl;
$R_2$–$R_4$=halogen, alkoxy, opt. substd. alkyl, aryl, alkenyl, or alkynyl, provided that one of $R_2$–$R_4$ is halogen;
Y=a leaving gp.;
$R_5$–$R_7$=alkoxycarbonyl, alkoxy, cyano, acyl, H, opt. substd. alkyl, aryl, alkenyl, or alkynyl;
$R_5$ and $R_6$, or $R_5$ and $R_7$ together with the adjacent carbon atom may form an opt. substd. ring;
provided that when $R_1$ is aryl, then $R_5$ and $R_7$ together with the carbon atom do not form an aryl ring.

U.S. Pat. No. 5,691,373 covers nonpeptide endothelin antagonists of formula

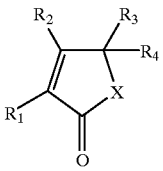
I or a tautomeric open chain ketoacid form thereof or a pharmaceutically acceptable salt thereof wherein $R_1$ is cycloalkyl substituted or unsubstituted of from 3 to 12 carbon atoms,
phenyl substituted with from 1 to 5 substituents,
naphthyl unsubstituted or substituted with from 1 to 5 substituents, or
heteroaryl unsubstituted or substituted with from 1 to 5 substituents;
$R_2$ is alkyl substituted or unsubstituted straight,
or branched of from 1 to 12 carbon atoms,
cycloalkyl substituted or unsubstituted of from 3 to 12 carbon atoms,
aryl which is unsubstituted or substituted with from 1 to 5 substituents,
heteroaryl which is unsubstituted or substituted with from 1 to 3 substituents;
$R_3$ is alkyl substituted or unsubstituted straight, or branched, of from 1 to 12 carbon atoms,
cycloalkyl substituted or unsubstituted of from 3 to 12 carbon atoms,
aryl which is unsubstituted or substituted with from 1 to 5 substituents,
heteroaryl which is unsubstituted or substituted with from 1 to 3 substituents;
$R_4$ is hydroxy or $OR_5$,
$SR_5$, wherein $R_5$ is alkyl or substituted alkyl of from 1 to 7 carbon atoms, or
$(CH_2)_nOR_5$ wherein n is an integer of from 1 to 3;
X is O or S;
with the proviso that when $R_1$ is monosubstituted phenyl and the substituent is p-methoxy, $R_3$ is not unsubstituted phenyl, monosubstituted phenyl, or mesityl and with the further proviso when $R_2$ is alkyl substituted, the substituent is not oxygen at the α-position to the furanone ring.

This application for patent is hereby incorporated by reference.

Compounds of formula

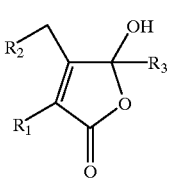
IA wherein:

| R₁ | R₂ | R₃ |
|---|---|---|
| phenyl | phenyl | phenyl |
| phenyl | phenyl | p-chlorophenyl |
| phenyl | phenyl | p-bromophenyl |
| piperonyl 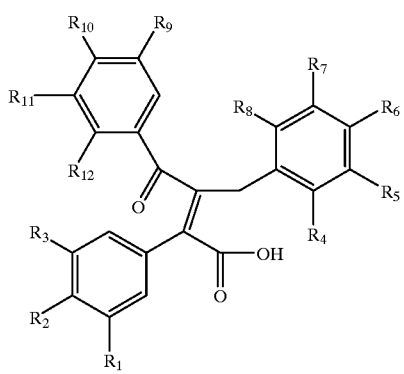 | phenyl | p-chlorophenyl |
| phenyl | o-chlorophenyl | phenyl |
| phenyl | phenyl | p-phenylphenyl |
| anisyl (p-methoxyphenyl) | phenyl | phenyl |
| anisyl | α-furyl | phenyl |
| phenyl | piperonyl | p-chlorophenyl |
| anisyl | o-chlorophenyl | phenyl |
| anisyl | o-methoxyphenyl | phenyl |
| phenyl | phenyl | mesityl |
| phenyl | phenyl | p-methylphenyl |
| phenyl | o-chlorophenyl | p-chlorophenyl |
| phenyl | phenyl | p-methoxyphenyl |
| anisyl | o-methylphenyl | phenyl |
| phenyl | piperonyl | p-bromophenyl |
| phenyl | piperonyl | p-methoxyphenyl | are all known. However, the methods of using 2(5H)-furanone, 3-(1,3-benzodioxol-5-yl)-5-(4-chlorophenyl)-5-hydroxy-4-(phenylmethyl)- and a pharmaceutical composition containing it are taught in the above co-pending application.

SUMMARY OF THE INVENTION

The instant invention is a compound of Formula I

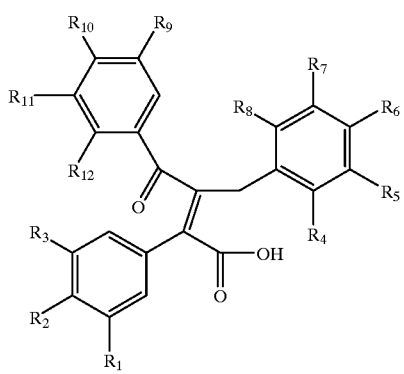

I or a pharmaceutically acceptable salt thereof wherein:
$R_1$ is hydrogen,
  alkyl,
  alkoxy,
  O-allyl, or
  O-alkyl;
$R_2$ is hydrogen or
  alkoxy;
$R_3$ is hydrogen,
  alkyl, or
  alkoxy; or
$R_2$ and $R_3$ together form
  —O—CH₂—O— or
  —O—CH₂—CH₂—O—;
$R_4$ is hydrogen or
  alkoxy;
$R_5$ is hydrogen,
  alkoxy, or
  O-allyl;
$R_6$ is hydrogen,
  alkoxy, or
  O-allyl;
$R_7$ is hydrogen,
  alkoxy,
  O-allyl,
  NH₂,
  —NHMe,
  —NHEt,
  —N(Me)₂,
  —N(Et)₂,

wherein n is an integer of from 4 to 5,

—O(CH$_2$)$_m$COOH,

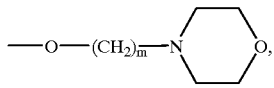

—O(CH$_2$)$_m$N(Me)$_2$,

—O(CH$_2$)$_m$SO$_3$H, or

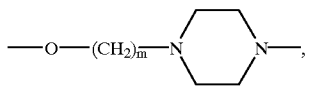

wherein m is an integer of from 2 to 5;
R$_5$ and R$_6$ together can form —O—CH$_2$—O—;
R$_6$ and R$_7$ together can form —O—CH$_2$—O—;
R$_8$ is hydrogen or
    alkoxy;
R$_9$ is hydrogen,
    alkyl, or
    alkoxy;
R$_{10}$ is alkoxy or
    amino;
R$_{10}$ and R$_9$ together form —O—CH$_2$—O—;
R$_{11}$ is hydrogen,
    alkyl, or
    alkoxy; and
R$_{12}$ is hydrogen or
    alkoxy.

Preferred compounds of the invention are those of Formula I above wherein
R$_1$ is hydrogen,
    methyl,
    methoxy, or
    O-allyl;
R$_2$ is hydrogen or
    methoxy;
R$_3$ is hydrogen,
    methyl, or
    methoxy;
R$_2$ and R$_3$ form
    —O—CH$_2$—O— or
    —O—CH$_2$—CH$_2$—O—;
R$_4$ is hydrogen or
    methoxy;
R$_5$ is hydrogen,
    methoxy, or
    ethoxy;
R$_6$ is methoxy,
    ethoxy, or
    O-allyl;
R$_7$ is methoxy,
    ethoxy,
    —NH$_2$,
    —NHMe,
    —NHEt,
    —N(Me)$_2$,
    —N(Et)$_2$,

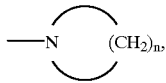

wherein n is an integer of from 4 to 5,
—O(CH$_2$)$_m$COOH,

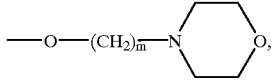

—O(CH$_2$)$_m$N(Me)$_2$,

—O(CH$_2$)$_m$SO$_3$H, or

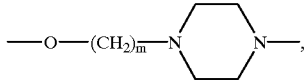

wherein m is an integer of from 2 to 5;
R$_8$ is hydrogen;
R$_9$ is hydrogen,
    methyl, or
    methoxy;
R$_{10}$ is methoxy,
    ethoxy, or
    —N(CH$_3$)$_2$;
R$_{10}$ and R$_9$ together form —O—CH$_2$—O—;
R$_{11}$ is hydrogen,
    methyl, or
    methoxy; and
R$_{12}$ is hydrogen or
    methoxy.

Still more preferred compounds of the invention are those of Formula I above wherein
R$_1$ is hydrogen or
    methoxy;
R$_2$ is methoxy;
R$_3$ is hydrogen or
    methoxy; or
R$_2$ and R$_3$ together form —O—CH$_2$—O—;
R$_4$ is hydrogen;
R$_5$ is hydrogen or
    methoxy;
R$_6$ is methoxy;
R$_7$ is methoxy; or
R$_6$ and R$_7$ together form —O—CH$_2$—O—;
R$_8$ is hydrogen;
R$_9$ is hydrogen,
    methyl, or
    methoxy;
R$_{10}$ is methoxy or
    ethoxy;
R$_{11}$ is hydrogen or
    methoxy; or
R$_{12}$ is hydrogen.

Yet still more preferred compounds of the invention are those of Formula I above wherein
(E)-2-(3,5-Dimethoxy-phenyl)-4-(4-methoxy-phenyl)-4-oxo-3-(3,4,5-trimethoxy-benzyl)-but-2-enoic acid;
(E)-2-Benzo[1,3]dioxol-5-yl-4-(4-methoxy-3-methyl-phenyl)-4-oxo-3-(3,4,5-trimethoxy-benzyl)-but-2-enoic acid;

(E)-2-(7-Methoxy-benzo[1,3]dioxol-5-yl)-4-(4-methoxy-phenyl)-4-oxo-3-(3,4,5-trimethoxy-benzyl)-but-2-enoic acid;

(E)-2-Benzo[1,3]dioxol-5-yl-3-(4-ethoxy-carbonylmethoxy-3,5-dimethoxy-benzyl)-4-(4-methoxy-phenyl)-4-oxo-but-2-enoic acid;

(E)-4-Benzo[1,3]dioxol-5-yl-2-(7-methoxy-benzo[1,3]dioxol-5-yl)-4-oxo-3-(3,4,5-trimethoxy-benzyl)-but-2-enoic acid;

(E)-3-(3-Allyloxy-4,5-dimethoxy-benzyl)-2-benzo[1,3]dioxol-5-yl-4-(4-methoxy-phenyl)-4-oxo-but-2-enoic acid;

(E)-2-Benzo[1,3]dioxol-5-yl-3-(3-ethoxy-4,5-dimethoxy-benzyl)-4-(4-methoxy-phenyl)-4-oxo-but-2-enoic acid;

(E)-2-Benzo[1,3]dioxol-5-yl-4-(2,4-dimethoxy-phenyl)-4-oxo-3-(3,4,5-trimethoxy-benzyl)-but-2-enoic acid;

(E)-2-(7-Allyloxy-benzo[1,3]dioxol-5-yl)-4-(4-methoxy-phenyl)-4-oxo-3-(3,4,5-trimethoxy-benzyl)-but-2-enoic acid;

(E)-2-Benzo[1,3]dioxol-5-yl-4-oxo-3-(3,4,5-trimethoxy-benzyl)-4-(3,4,5-trimethoxy-phenyl)-but-2-enoic acid;

(E)-2-Benzo[1,3]dioxol-5-yl-3-(4-ethoxy-3,5-dimethoxy-benzyl)-4-(4-methoxy-phenyl)-4-oxo-but-2-enoic acid;

(E)-3-(4-Allyloxy-3, 5-dimethoxy-benzyl)-2-benzo[1,3]dioxol-5-yl-4-(4-methoxy-phenyl)-4-oxo-but-2-enoic acid;

(E)-2-Benzo[1,3]dioxol-5-yl-4-(4-methoxy-phenyl)-4-oxo-3-(3,4,5-triethoxy-benzyl)-but-2-enoic acid;

(E)-2-Benzo[1,3]dioxol-5-yl-3-(7-methoxy-benzo[1,3]dioxol-5-ylmethyl)-4-(4-methoxy-phenyl)-4-oxo-but-2-enoic acid;

(E)-2-Benzo[1,3]dioxol-5-yl-3-(3,4-bis-allyloxy-5-methoxy-benzyl)-4-(4-methoxy-phenyl)-4-oxo-but-2-enoic acid;

(E)-2-Benzo[1,3]dioxol-5-yl-4-(3,4-dimethoxy-phenyl)-4-oxo-3-(3,4,5-trimethoxy-benzyl)-but-2-enoic acid;

(E)-2-Benzo[1,3]dioxol-5-yl-3-(3-dimethylamino-benzyl)-4-(4-methoxy-phenyl)-4-oxo-but-2-enoic acid;

(E)-2-Benzo[1,3]dioxol-5-yl-3-[3-(3-carboxy-propoxy)-4,5-dimethoxy-benzyl]-4-(4-methoxy-phenyl)-4-oxo-but-2-enoic acid;

(E)-2-(3,5-Dimethyl-phenyl)-4-(4-methoxy-phenyl)-4-oxo-3-(3,4,5-trimethoxy-benzyl)-but-2-enoic acid;

(E)-2-Indan-5-yl-4-(4-methoxy-phenyl)-4-oxo-3-(3,4,5-trimethoxy-benzyl)-but-2-enoic acid;

(E)-2-Benzo[1,3]dioxol-5-yl-4-(4-ethoxy-3-methyl-phenyl)-4-oxo-3-(3,4,5-trimethoxy-benzyl)-but-2-enoic acid;

(E)-3-[3-(3-Carboxy-propoxy)-4,5-dimethoxy-benzyl]-2-(3,5-dimethyl-phenyl)-4-(4-methoxy-phenyl)-4-oxo-but-2-enoic acid;

(E)-2-Benzo[1,3]dioxol-5-yl-3-[3-(4-carboxy-butoxy)-4,5-dimethoxy-benzyl]-4-(4-methoxyphenyl)-4-oxo-but-2-enoic acid;

(E)-2-Benzo[1,3]dioxol-5-yl-3-[3,4-dimethoxy-5-(2-morpholin-4-yl-ethoxy)-benzyl]-4-(4-methoxy-phenyl)-4-oxo-but-2-enoic acid;

(E)-2-Benzo[1,3]dioxol-5-yl-3-[3-(3-dimethylamino-propoxy)-4,5-dimethoxy-benzyl]-4-(4-methoxy-phenyl)-4-oxo-but-2-enoic acid (E)-2-Benzo[1,3]dioxol-5-yl-3-[3,4-dimethoxy-5-(3-sulfo-propoxy)-benzyl]-4-(4-methoxy-phenyl)-4-oxo-but-2-enoic acid;

(E)-3-(3-Amino-benzyl)-2-benzo[1,3]dioxol-5-yl-4-(4-methoxy-phenyl)-4-oxo-but-2-enoic acid;

(E)-2-Benzo[1,3]dioxol-5-yl-4-(4-methoxy-phenyl)-3-(3-methylamino-benzyl)-4-oxo-but-2-enoic acid;

(E)-2-Benzo[1,3]dioxol-5-yl-3-[3-(2-dimethyl-amino-ethoxy)-4,5-dimethoxy-benzyl]-4-(4-methoxy-phenyl)-4-oxo-but-2-enoic acid;

(E)-2-Benzo[1,3]dioxol-5-yl-3-[3,4-dimethoxy-5-(3-morpholin-4-yl-propoxy)-benzyl]-4-(4-methoxy-phenyl)-4-oxo-but-2-enoic acid;

(E)-2-Benzo[1,3]dioxol-5-yl-3-{3,4-dimethoxy-5-[3-(4-methyl-piperazin-1-yl)-propoxy]-benzyl}-4-(4-methoxy-phenyl)-4-oxo-but-2-enoic acid;

(E)-4-(4-Amino-phenyl)-2-benzo[1,3]dioxol-5-yl-4-oxo-3-(3,4,5-trimethoxy-benzyl)but-2-enoic acid; and (E)-2-Benzo[1,3]dioxol-5-yl-4-(4-dimethyl-amino-phenyl)-4-oxo-3-(3,4,5-trimethoxy-benzyl)-but-2-enoic acid.

The most preferred compounds of the invention are selected from (E)-2-Benzo[1,3]dioxol-5-yl-4-(4-methoxy-phenyl)-4-oxo-3-(3,4,5-trimethoxy-benzyl)-but-2-enoic acid;

(E)-3-Benzo[1,3]dioxol-5-ylmethyl-2-(4-methoxy-phenyl)-4-oxo-4-(3,4,5-trimethoxy-phenyl)-but-2-enoic acid; and (E)-4-(4-Ethoxy-3-methyl-phenyl)-2-(7-methoxy-benzo[1,3]dioxol-5-yl)-4-oxo-3-(3,4,5-trimethoxy-benzyl)-but-2-enoic acid.

Elevated levels of endothelin have been shown to be involved in a number of pathophysiological states including angina, arrhythmias, asthma, atherosclerosis, benign prostatic hyperplasia, Buerger's Disease, cardiac arrest, cardiogenic shock, cerebral trauma, Chrohn's Disease, congenital heart disease, congestive heart failure (CHF) (mild), congestive heart failure (CHF) (severe), cerebral ischemia, cerebral infarction, cerebral vasospasm, cirrhosis, diabetes, dilated cardiomyopathy, drowning (anoxia), endotoxic shock, gastric mucosal damage, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasu's arteritis, ulcerative colitis, uremia after hemodialysis, and uremia before hemodialysis. As antagonists of endothelin, the compounds of Formula I are useful in their treatment.

A still further embodiment of the present invention is a pharmaceutical composition for administering a therapeutically effective amount of a compound of Formula I in unit dosage form in the treatment methods mentioned above.

Finally, the present invention is directed to methods for production of a compound of Formula I.

DETAILED DESCRIPTION OF THE INVENTION

The present invention covers compound of Formula I above and its pharmaceutically acceptable salts.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, isethionic, and the like. Also contemplated are salts of amino acids such as lysinate, arginate, and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloro-procaine, choline, diethanolamine, piperazine, dicyclohexylamine, ethylenediamine, N-methylglucamine, and procaine (see, for example, Berge S. M., et al., "Pharmaceutical Salts," *Journal of Pharmaceutical Science*, 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention are all trans; not cis in each of the specifically named compounds.

The terms used to describe the compounds of Formula I are as follows.

The term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl. The alkyl group is unsubstituted or substituted by from 1 to 6 substituents selected from alkyl, alkoxy, thioalkoxy all as defined herein, hydroxy, thiol, nitro, halogen, amino, monosubstituted amino, disubstituted amino, formyl, cycloalkyl, carboxyl, nitride,

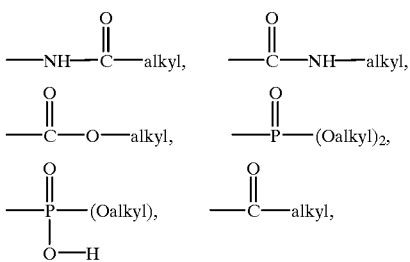

aryl, or heteroaryl wherein alkyl, aryl, and heteroaryl are defined as herein.

The term "cycloalkyl" means a saturated hydrocarbon ring which contains from 3 to 12 carbon atoms unless otherwise specified, for example, cyclopropyl, cyclobutyl, cyclopentyl, cyclohexyl, cycloheptyl, and adamantyl. The cycloalkyl ring may be unsubstituted or substituted by from 1 to 3 substituents selected from alkyl, cycloalkyl, cycloalkoxy, alkoxy, thioalkoxy all as defined herein, hydroxy, thiol, nitro, halogen, amino, monosubstituted amino, disubstituted amino, formyl, carboxyl, nitrile, alkylsulfoxyl, arylsulfoxyl, alkylsulfonyl, arylsulfonyl,

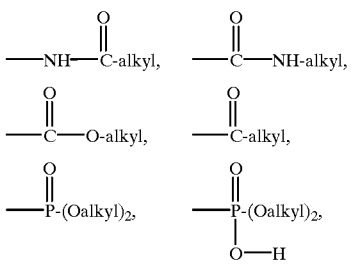

aryl, or heteroaryl wherein alkyl, aryl, and heteroaryl are defined as herein.

The terms "alkoxy" and "thioalkoxy" are O-alkyl or S-alkyl as defined above for alkyl.

Two alkoxy or thioalkoxy groups can be taken together to form a cyclic group such as

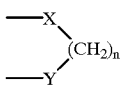

where X and Y are independently either O or S and n is 1, 2, 3, or 4.

The term "aryl" means an aromatic radical which is a phenyl group, a benzyl group, a naphthyl group, a biphenyl group, a pyrenyl group, an anthracenyl group, or a fluorenyl group and the like, unsubstituted or substituted by 1 to 5 substituents selected from alkyl as defined above, alkoxy as defined above, thioalkoxy as defined above, hydroxy, thiol, nitro, halogen, amino, monosubstituted amino, disubstituted amino, formyl, carboxy, nitrile, arylsulfoxyl, alkylsulfoxyl, arylsulfonyl, alkylsulfonyl,

-continued

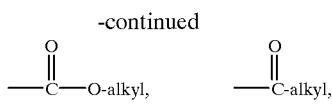

aryl, or heteroaryl wherein alkyl, aryl, and heteroaryl are defined as above.

The term "heteroaryl" means a heteroaromatic radical which is 2-or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 3 substituents selected from alkyl as defined above, aryl as defined above, alkoxy as defined above, thioalkoxy as defined above, hydroxy, thiol, nitro, halogen, formyl, amino, monosubstituted amino, disubstituted amino, carboxyl, nitrile,

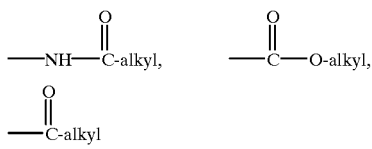

wherein alkyl is as defined above or phenyl.

"Halogen" is fluorine, chlorine, bromine or iodine.

The following radioligand binding assays were used (Reynolds E. E., Keiser J. A., Haleen S. J., Walker D. M., Davis L. S., Olszewski B., Taylor D. G., Hwang O., Welch K. M., Flynn M. A., Thompson D. M., et al., *J. Pharmacol. Exp. Ther.*, 1995;273:1410–1417).

The following cultured cells were used in binding experiments: CHO-K1 cells expressing recombinant human $ET_BR$ (HERBA B), or Ltk$^-$ cells expressing human $ET_AR$ (HERBA A). Each of these cell types expressed a homogeneous population of the designated ET receptor subtype, which displayed canonical $ET_AR$ or $ET_BR$ pharmacology. Membranes were prepared from cultured cells by lysing cells in cold lysis buffer (5 mM HEPES, 2 mM EDTA, pH 7.4) and homogenizing with a Dounce "A" homogenizer. All of the homogenates were centrifuged at 30,000×g for 20 minutes at 4° C. Membrane pellets were resuspended in cold buffer containing 20 mM Tris, 2 mM EDTA, 200 µM Pefablock, 10 µM phosphoramidon, 10 µM leupeptin, and 1 µM pepstatin (pH 7.4) and frozen at −80° C. until use. Radioligand and competing ligands were prepared in binding buffer containing 20 mM Tris, 2 mM EDTA, and 0.1% BSA.

Competition binding assays were initiated by combining membranes, [$^{125}$I]-ET-1 (40 pM) and competing ligand in a final volume of 250 µL and incubating for 2 hours at 37° C. The assay was terminated by filtration over Whatman GF/B filters that were presoaked with 50 mM Tris, pH 7.4, containing 0.2% BSA and 100 µM bacitracin. Nonspecific binding was defined as total binding minus nonspecific binding. Specific binding was analyzed by nonlinear least squared curve fitting (InPlot, GraphPad Software, San Diego, Calif.), and the estimated $IC_{50}$ value was used to calculate $K_i$ according to the method of Cheng and Prusoff (1973).

The data in Table 2 below shows the endothelin receptor binding and antagonist activity of representative compounds of the instant invention.

TABLE 2

| Example | HERBA-A[a] | HERBA-B[a] |
|---------|------------|------------|
| 1       | 65         | >2500      |
| 2       | 58         | 10000      |
| 3       | 70         | >2500      |

[a]$IC_{50}$ values in nM

As can be seen in Table 2 above, the compounds of Formula I bind to the endothelin receptors $ET_A$ (HERBA-A) in the µM to nM range.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions and/or any of the additions generally regarded as safe. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Compounds of Formula I may be prepared as in Scheme I. The alpha-hydroxybutenolide is dissolved in a solvent such as methanol or methanol and water, and reacted with one or more equivalents of a suitable base. The solution is (1) exposed to a ultraviolet light source for a sufficient time, and is (2) acidified and isolated from the solution as the compound in Formula I.

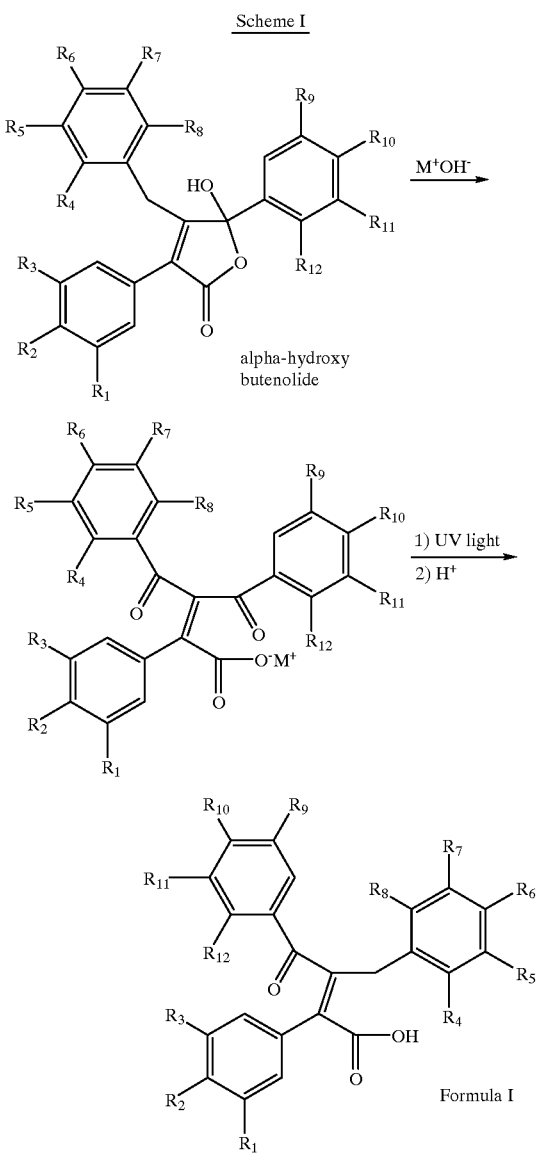

Scheme I

EXAMPLE 1

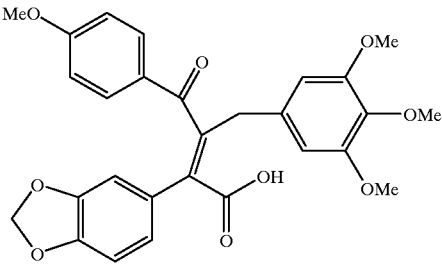

(E)-2-Benzo[1,3]dioxol-5-yl-4-(4-methoxy-phenyl)-4-oxo-3-(3,4,5-trimethoxy-benzyl)-but-2-enoic acid To 150 mL methanol to which 3.95 mL 1.00N NaOH had been added was added 3-benzo[1,3]dioxol-5-yl-5-hydroxy-5-(4-methoxyphenyl)-4-(3,4,5-trimethoxy-benzyl)-5H-furan-2-one 2.00 g (3.95 mmol). The suspension was stirred to give solution and was placed in a 400 mL Pyrex™ beaker and diluted with 150 mL water. The beaker was covered with a quartz evaporating dish (100 mm o.d.×15 mm h., QRD 100; Quartz Scientific, Inc., Fairport Harbor, Ohio). The covered solution was irradiated for 30 hours in an Atlas Sunchex™ simulated sunlight exposure instrument (Xenon arc lamp, set to 0.35 W/m² at 340 nm, filtered to exclude wavelengths less than 280 nm; Atlas Electric Devices Co., Chicago, Ill.). The mixture was filtered to remove insoluble solids, and the filtrate was evaporated in vacuo to remove methanol. The residual aqueous solution was extracted repeatedly with ethyl ether, while the pH of the aqueous phase was adjusted incrementally between 7.5 and 8 by addition of 3N HCl. The aqueous phase was then acidified to pH 1 with HCl and extracted with ethyl ether. The ether phase was washed with saturated sodium chloride solution and dried over anhydrous magnesium sulfate. Addition of petroleum ether gave a crystalline solid which was filtered and dried under vacuum at 40° C., giving a solid melting at 192–193° C., 180 mg. The product was identified by $^1$H NMR, MS, [M–H]$^+$=505.3 Da. and microanalysis.

chromatography on 50 g silica gel eluted with 1% methanol in chloroform. The appropriate fractions were evaporated to a solid, 0.77 g. The product was identified by $^1$H NMR, MS [M–H]$^+$=505.4 Da. and microanalysis.

EXAMPLE 3

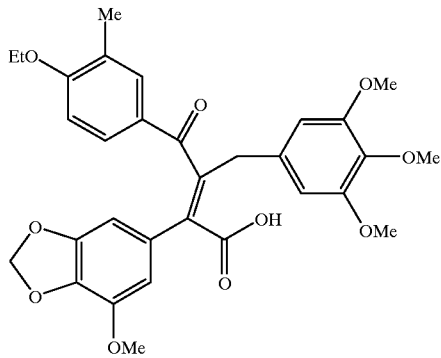

(E)-4-(4-Ethoxy-3-methyl-benzoyl)-2-(7-methoxy-benzo[1,3]dioxol-5-yl)-4-(3,4,5-trimethoxy-benzyl)-but-2-enoic acid To 150 mL methanol to which 4.2 mL 1.00N NaOH had been added was added 3-(7-methoxy-benzo[1,3]dioxol-5-yl)-5-hydroxy-5-(4-ethoxy-3-methylphenyl)-4-(3,4,5-trimethoxy-benzyl)-5H-furan-2-one 2.00 g (3.95 mmol). The suspension was stirred to give solution and was placed in a 400 mL Pyrex™ beaker and diluted with 150 mL water. The beaker was covered with a quartz evaporating dish (100 mm o.d.×15 mm h., QRD 100; Quartz Scientific, Inc., Fairport Harbor, Ohio). The covered solution was irradiated for 20 hours in an Atlas Sunchex™ simulated sunlight exposure instrument (Xenon arc lamp, set to 0.35 W/m² at 340 nm, filtered to exclude wavelengths less than 280 nm; Atlas Electric Devices Co., Chicago, Ill.). The mixture was filtered to remove insoluble solids, and the filtrate was evaporated in vacuo to remove methanol. The residual aqueous solution was extracted repeatedly with ethyl ether, while the pH of the aqueous phase was adjusted incrementally between 7.5 and 8 by addition of 3N HCl. The aqueous phase was then acidified to pH 1 with HCl and extracted with ethyl ether. The ether phase was washed with saturated sodium chloride solution and dried over anhydrous magnesium sulfate. Evaporation of the ether solution under reduced pressure gave a yellow solid, 340 mg. The residue was purified by chromatography on 50 g silica gel eluted with a gradient of 0% to 3% methanol in chloroform. The appropriate fractions were evaporated to a solid, 0.232 g. The product was identified by $^1$H NMR, MS, [M–H]$^+$=505.3 Da. and microanalysis.

By a process similar to that of Example 3, Examples 4 through 36 are prepared.

EXAMPLE 2

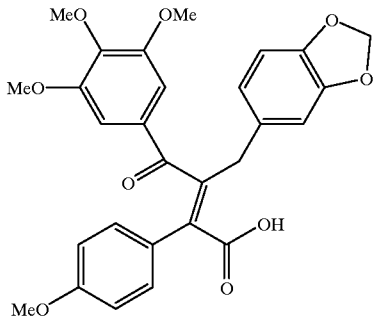

(E)-3-Benzo[1,3]dioxol-5-ylmethyl-2-(4-methoxy-phenyl)-4-oxo-4-(3,4,5-trimethoxy-phenyl)-but-2-enoic acid To 250 mL methanol was added 4-benzo[1,3]dioxol-5-ylmethyl-5-hydroxy-3-(4-methoxy-phenyl)-5-(3,4,5-trimethoxy-phenyl)-5H-furan-2-one 4.0 g (7.89 mmol), giving solution. To the solution was added 250 mL water containing 15.8 mL 1.001N NaOH. The solution was irradiated with a Hanovia ultraviolet light contained in a quartz reactor (Ace Glass, Catalog 1200, #7840-180) for 16 hours at ambient temperature. The solution was evaporated in vacuo to remove the methanol. The residual aqueous solution was extracted repeatedly with ethyl ether, while the pH of the aqueous phase was adjusted incrementally between 7.5 and 8 by addition of 3N HCl. The aqueous phase was then acidified to pH 1 with HCl and extracted with ethyl ether. The ether extract was washed with saturated sodium chloride solution and dried over anhydrous magnesium sulfate. Evaporation of the ether solution under reduced pressure gave a foam, 1.44 g. The residue was purified by

EXAMPLE 4
(E)-2-(3,5-Dimethoxy-phenyl)-4-(4-methoxy-phenyl)-4-oxo-3-(3,4,5-trimethoxy-benzyl)-but-2-enoic acid

EXAMPLE 5
(E)-2-Benzo[1,3]dioxol-5-yl-4-(4-methoxy-3-methyl-phenyl)-4-oxo-3-(3,4,5-trimethoxy-benzyl)-but-2-enoic acid

Example 6
(E)-2-(7-Methoxy-benzo[1,3]dioxol-5-yl)-4-(4-methoxy-phenyl)-4-oxo-3-(3,4,5-trimethoxy-benzyl)-but-2-enoic acid

EXAMPLE 7
(E)-2-Benzo[1,3]dioxol-5-yl-3-(4-ethoxycarbonylmethoxy-3,5-dimethoxy-benzyl)-4-(4-methoxy-phenyl)-4-oxo-but-2-enoic acid

EXAMPLE 8
(E)-4-Benzo[1,3]dioxol-5-yl-2-(7-methoxy-benzo 1,3]-dioxol-5-yl)-4-oxo-3-(3,4,5-trimethoxy-benzyl)-but-2-enoic acid

EXAMPLE 9
(E)-3-(3-Allyloxy-4,5-dimethoxy-benzyl)-2-benzo[1,3]-dioxol-5-yl-4-(4-methoxy-phenyl)-4-oxo-but-2-enoic acid

EXAMPLE 10
(E)-2-Benzo[1,3]dioxol-5-yl-3-(3-ethoxy-4,5-dimethoxy-benzyl)-4-(4-methoxy-phenyl)-4-oxo-but-2-enoic acid

Example 11
(E)-2-Benzo[1,3]dioxol-5-yl-4-(2,4-dimethoxy-phenyl)-4-oxo-3-(3,4,5-trimethoxy-benzyl)-but-2-enoic acid

EXAMPLE 12
(E)-2-(7-Allyloxy-benzo[1,3]dioxol-5-yl)-4-(4-methoxy-phenyl)-4-oxo-3-(3,4,5-trimethoxy-benzyl)-but-2-enoic acid

EXAMPLE 13
(E)-2-Benzo[1,3]dioxol-5-yl-4-oxo-3-(3,4,5-trimethoxy-benzyl)-4-(3,4,5-trimethoxy-phenyl)-but-2-enoic acid

EXAMPLE 14
(E)-2-Benzo[1,3]dioxol-5-yl-3-(4-ethoxy-3,5-dimethoxy-benzyl)-4-(4-methoxy-phenyl)-4-oxo-but-2-enoic acid

EXAMPLE 15
(E)-3-(4-Allyloxy-3,5-dimethoxy-benzyl)-2-benzo[1,3]-dioxol-5-yl-4-(4-methoxy-phenyl)-4-oxo-but-2-enoic acid

EXAMPLE 16
(E)-2-Benzo[1,3]dioxol-5-yl-4-(4-methoxy-phenyl)-4-oxo-3-(3,4,5-triethoxy-benzyl)-but-2-enoic acid

EXAMPLE 17
(E)-2-Benzo[1,3]dioxol-5-yl-3-(7-methoxy-benzo[1,3]-dioxol-5-ylmethyl)-4-(4-methoxy-phenyl)-4-oxo-but-2-enoic acid

EXAMPLE 18
(E)-2-Benzo[1,3]dioxol-5-yl-3-(3,4-bis-allyloxy-5-methoxy-benzyl)-4-(4-methoxy-phenyl)-4-oxo-but-2-enoic acid

EXAMPLE 19
(E)-2-Benzo[1,3]dioxol-5-yl-4-(3,4-dimethoxy-phenyl)-4-oxo-3-(3,4,5-trimethoxy-benzyl)-but-2-enoic acid

EXAMPLE 20
(E)-2-Benzo[1,3]dioxol-5-yl-3-(3-dimethylamino-benzyl)-4-(4-methoxy-ihenyl)-4-oxo-but-2-enoic acid

EXAMPLE 21
(E)-2-Benzo[1,3]dioxol-5-yl-3-[3-(3-carboxy-propoxy)-4,5-dimethoxy-benzyl]-4-(4-methoxy-phenyl)-4-oxo-but-2-enoic acid

EXAMPLE 22
(E)-2-(3,5-Dimethyl-phenyl)-4-(4-methoxy-phenyl)-4-oxo-3-(3,4,5-trimethoxy-benzyl)-but-2-enoic acid

EXAMPLE 23
(E)-2-Indan-5-yl-4-(4-methoxy-phenyl)-4-oxo-3-(3,4,5-trimethoxy-benzyl)-but-2-enoic acid

EXAMPLE 24
(E)-2-Benzo[1,3]dioxol-5-yl-4-(4-ethoxy-3-methyl-phenyl)-4-oxo-3-(3,4,5-trimethoxy-benzyl)-but-2-enoic acid

EXAMPLE 25
(E)-3-[3-(3-Carboxy-propoxy)-4,5-dimethoxy-benzyl]-2-(3,5-dimethyl-phenyl)-4-(4-methoxy-phenyl)-4-oxo-but-2-enoic acid

EXAMPLE 26
(E)-2-Benzo[1,3]dioxol-5-yl-3-[3-(4-carboxy-butoxy)-4,5-dimethoxy-benzyl]-4-(4-methoxy-phenyl)-4-oxo-but-2-enoic acid

EXAMPLE 27
(E)-2-Benzo[1,3]dioxol-5-yl-3-[3,4-dimethoxy-5-(2-morpholin-4-yl-ethoxy)-benzyl]-4-(4-methoxy-phenyl)-4-oxo-but-2-enoic acid

EXAMPLE 28
(E)-2-Benzo[1,3]dioxol-5-yl-3-[3-(3-dimethylamino-propoxy)-4,5-dimethoxy-benzyl]-4-(4-methoxy-phenyl)-4-oxo-but-2-enoic acid

EXAMPLE 29
(E)-2-Benzo[1,3]dioxol-5-yl-3-[3,4-dimethoxy-5-(3-sulfo-propoxy)-benzyl]-4-(4-methoxy-phenyl)-4-oxo-but-2-enoic acid

EXAMPLE 30
(E)-3-(3-Amino-benzyl)-2-benzo[1,3]dioxol-5-yl-4-(4-methoxy-phenyl)-4-oxo-but-2-enoic acid

EXAMPLE 31
(E)-2-Benzo[1,3]dioxol-5-yl-4-(4-methoxy-phenyl)-3-(3-methylamino-benzyl)-4-oxo-but-2-enoic acid

EXAMPLE 32
(E)-2-Benzo[1,3]dioxol-5-yl-3-[3]-(2-dimethylamino-ethoxy)-4,5-dimethoxy-benzyl-4-(4-methoxy-phenyl)-4-oxo-but-2-enoic acid

EXAMPLE 33
(E)-2-Benzo[1,3]dioxol-5-yl-3-[3,4-dimethoxy-5-(3-morpholin-4-yl-propoxy)-benzyl]-4-(4-methoxy-phenyl)-4-oxo-but-2-enoic acid

EXAMPLE 34
(E)-2-Benzo[1,3]dioxol-5-yl-3-{3,4-dimethoxy-5-[3-(4-methyl-piperazin-1-yl)-propoxy]-benzyl}-4-(4-methox-phenyl)-4-oxo-but-2-enoic acid

EXAMPLE 35
(E)-4-(4-Amino-phenyl)-2-benzo[1,3]dioxol-5-yl-4-oxo-3-(3,4,5-trimethoxy-benzyl)but-2-enoic acid

EXAMPLE 36
(E)-2-Benzo[3]dioxol-5-yl-4-(4-dimethylamino-phenyl)-4-oxo-3-(3,4,5-trimethoxy-benzyl)-but-2-enoic acid.

We claim:
1. A process for the preparation of trans keto acids of Formula I

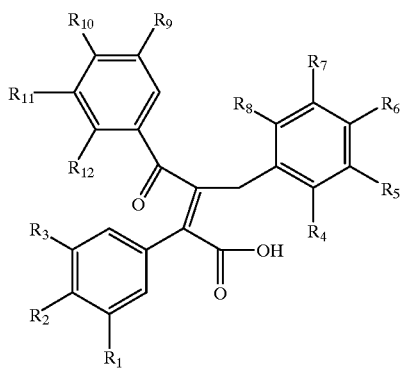

or a pharmaceutically acceptable salt thereof wherein:
$R_1$ is hydrogen,
  alkyl,
  alkoxy,
  O-allyl, or
  O-alkyl,
$R_2$ is hydrogen or
  alkoxy;
$R_3$ is hydrogen,
  alkyl, or
  alkoxy, or
$R_2$ and $R_3$ together form
  —O—CH$_2$—O— or
  —O—CH$_2$—CH$_2$—O—;
$R_4$ is hydrogen or
  alkoxy;
$R_5$ is hydrogen,
  alkoxy, or
  O-allyl;
$R_6$ is hydrogen,
  alkoxy, or
  O-allyl;
$R_7$ is hydrogen,
  alkoxy,
  O-allyl,
  —NH$_2$,
  —NHMe,
  —NHEt,
  —N(Me)$_2$,
  —N(Et)$_2$,

wherein n is an integer of from 4 to 5,
  —O(CH$_2$)$_m$COOH,

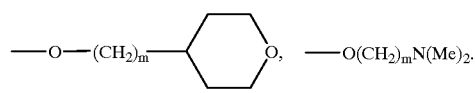

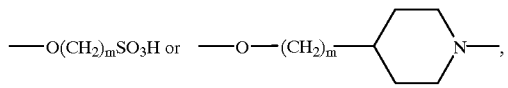

wherein m is an integer of from 2 to 5;
$R_5$ and $R_6$ together can form —O—CH$_2$—O—;
$R_6$ and $R_7$ together can form —O—CH$_2$—O—;
$R_8$ is hydrogen, or
  alkoxy;
$R_9$ is hydrogen,
  alkyl, or
  alkoxy;
$R_{10}$ is alkoxy or
  amino;
$R_{10}$ and $R_9$ together can form —O—CH$_2$—O—;
$R_{11}$ is hydrogen,
  alkyl, or
  alkoxy; and
$R_{12}$ is hydrogen or
  alkoxy
which are useful in treating conditions caused by elevated levels of endothelin which comprises
  1) dissolving a α-hydroxy butenolide of Formula II

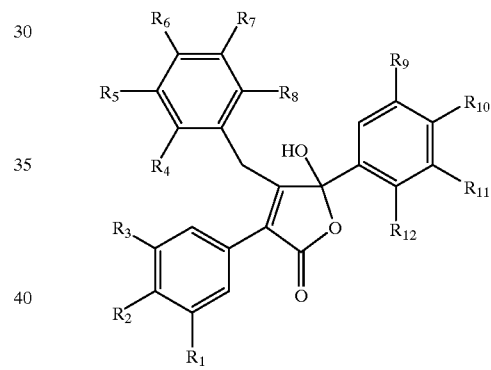

in a solvent;
  2) reacting it with one or more equivalents of a suitable base;
  3) exposing the solution from Step 2) above to an ultraviolet light source for a sufficient time, acidifying it, and isolating a compound of Formula I above from the solution.

2. A process according to claim 1 wherein:
$R_1$ is hydrogen,
  methyl,
  methoxy, or
  O-allyl;
$R_2$ is hydrogen or
  methoxy;
$R_3$ is hydrogen,
  methyl, or
  methoxy;
$R_2$ and $R_3$ form
  —O—CH$_2$—O— or
  —O—CH$_2$—CH$_2$—O—;
$R_4$ is hydrogen or
  methoxy;

R₅ is hydrogen,
  methoxy, or
  ethoxy;
R₆ is methoxy,
  ethoxy, or
  O-allyl;
R₇ is methoxy,
  ethoxy,
  O-allyl,
  —NH₂,
  —NHMe,
  —NHEt,
  —N(Me)₂,
  —N(Et)₂,

wherein n is an integer of from 4 to 5,
—O(CH₂)ₘCOOH,

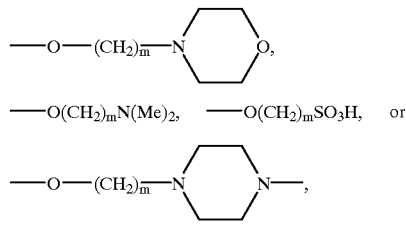

wherein m is an integer of from 2 to 5;
R₈ is hydrogen;
R₉ is hydrogen,
  methyl, or
  methoxy;
R₁₀ is methoxy,
  ethoxy, or
  —N(CH₃)₂;
R₁₀ and R₉ together form —O—CH₂—O—;
R₁₁ is hydrogen,
  methyl, or
  methoxy; and
R₁₂ is hydrogen or
  methoxy.

3. A process according to claim 1 wherein:
R₁ is hydrogen or
  methoxy;
R₂ is methoxy;
R₃ is hydrogen; or
R₂ and R₃ together form —O—CH₂—O—;
R₄ is hydrogen;
R₅ is hydrogen or
  methoxy;
R₆ is methoxy;
R₇ is methoxy; or
R₆ and R₇ together form —O—CH₂—O—;
R₈ is hydrogen;
R₉ is hydrogen,
  methyl, or
  methoxy;
R₁₀ is methoxy or
  ethoxy;
R₁₁ is hydrogen or
  methoxy; or
R₁₂ is hydrogen.

4. A compound selected from:
(E)-2-(3,5-Dimethoxy-phenyl)-4-(4-methoxy-phenyl)-4-oxo-3-(3,4,5-trimethoxy-benzyl)-but-2-enoic acid;
(E)-2-Benzo[1,3]dioxol-5-yl-4-(4-methoxy-3-methyl-phenyl)-4-oxo-3-(3,4,5-trimethoxy-benzyl)-but-2-enoic acid;
(E)-2-(7-Methoxy-benzo[1,3]dioxol-5-yl)-4-(4-methoxy-phenyl)-4-oxo-3-(3,4,5-trimethoxy-benzyl)-but-2-enoic acid;
(E)-2-Benzo[1,3]dioxol-5-yl-3-(4-ethoxy-carbonylmethoxy-3,5-dimethoxy-benzyl)-4-(4-methoxy-phenyl)-4-oxo-but-2-enoic acid;
(E)-4-Benzo[1,3]dioxol-5-yl-2-(7-methoxy-benzo[1,3]dioxol-5-yl)-4-oxo-3-(3,4,5-trimethoxy-benzyl)-but-2-enoic acid;
(E)-3-(3-Allyloxy-4,5-dimethoxy-benzyl)-2-benzo[1,3]dioxol-5-yl-4-(4-methoxy-phenyl)-4-oxo-but-2-enoic acid;
(E)-2-Benzo[1,3]dioxol-5-yl-3-(3-ethoxy-4,5-dimethoxy-benzyl)-4-(4-methoxy-phenyl)-4-oxo-but-2-enoic acid;
(E)-2-Benzo[1,3]dioxol-5-yl-4-(2,4-dimethoxy-phenyl)-4-oxo-3-(3,4,5-trimethoxy-benzyl)-but-2-enoic acid;
(E)-2-(7-Allyloxy-benzo[1,3]dioxol-5-yl)-4-(4-methoxy-phenyl)-4-oxo-3-(3,4,5-trimethoxy-benzyl)-but-2-enoic acid;
(E)-2-Benzo[1,3]dioxol-5-yl-4-oxo-3-(3,4,5-trimethoxy-benzyl)-4-(3,4,5-trimethoxy-phenyl)-but-2-enoic acid;
(E)-2-Benzo[1,3]dioxol-5-yl-3-(4-ethoxy-3,5-dimethoxy-benzyl)-4-(4-methoxy-phenyl)-4-oxo-but-2-enoic acid;
(E)-3-(4-Allyloxy-3,5-dimethoxy-benzyl)-2-benzo[1,3]dioxol-5-yl-4-(4-methoxy-phenyl)-4-oxo-but-2-enoic acid;
(E)-2-Benzo[1,3]dioxol-5-yl-4-(4-methoxy-phenyl)-4-oxo-3-(3,4,5-triethoxy-benzyl)-but-2-enoic acid;
(E)-2-Benzo[1,3]dioxol-5-yl-3-(7-methoxy-benzo[1,3]dioxol-5-ylmethyl)-4-(4-methoxy-phenyl)-4-oxo-but-2-enoic acid;
(E)-2-Benzo[1,3]dioxol-5-yl-3-(3,4-bis-allyloxy-5-methoxy-benzyl)-4-(4-methoxy-phenyl)-4-oxo-but-2-enoic acid;
(E)-2-Benzo[1,3]dioxol-5-yl-4-(3,4-dimethoxy-phenyl)-4-oxo-3-(3,4,5-trimethoxy-benzyl)-but-2-enoic acid;
(E)-2-Benzo[1,3]dioxol-5-yl-3-(3-dimethyl-amino-benzyl)-4-(4-methoxy-phenyl)-4-oxo-but-2-enoic acid;
(E)-2-Benzo[1,3]dioxol-5-yl-3-[3-(3-carboxy-propoxy)-4,5-dimethoxy-benzyl]-4-(4-methoxy-phenyl)-4-oxo-but-2-enoic acid;
(E)-2-(3,5-Dimethyl-phenyl)-4-(4-methoxy-phenyl)-4-oxo-3-(3,4,5-trimethoxy-benzyl)-but-2-enoic acid;
(E)-2-Indan-5-yl-4-(4-methoxy-phenyl)-4-oxo-3-(3,4,5-trimethoxy-benzyl)-but-2-enoic acid;
(E)-2-Benzo[1,3]dioxol-5-yl-4-(4-ethoxy-3-methyl-phenyl)-4-oxo-3-(3,4,5-trimethoxy-benzyl)-but-2-enoic acid;
(E)-3-[3-(3-Carboxy-propoxy)-4,5-dimethoxy-benzyl]-2-(3,5-dimethyl-phenyl)-4-(4-methoxy-phenyl)-4-oxo-but-2-enoic acid;
(E)-2-Benzo[1,3]dioxol-5-yl-3-[3-(4-carboxy-butoxy)-4,5-dimethoxy-benzyl]-4-(4-methoxyphenyl)-4-oxo-but-2-enoic acid;

(E)-2-Benzo[1,3]dioxol-5-yl-3-[3,4-dimethoxy-5-(2-morpholin-4-yl-ethoxy)-benzyl]-4-(4-methoxy-phenyl)-4-oxo-but-2-enoic acid;

(E)-2-Benzo[1,3]dioxol-5-yl-3-[3-(3-dimethyl-amino-propoxy)-4,5-dimethoxy-benzyl]-4-(4-methoxy-phenyl)-4-oxo-but-2-enoic acid (E)-2-Benzo[1,3]dioxol-5-yl-3-[3,4-dimethoxy-5-(3-sulfo-propoxy)-benzyl]-4-(4-methoxy-phenyl)-4-oxo-but-2-enoic acid;

(E)-3-(3-Amino-benzyl)-2-benzo[1,3]dioxol-5-yl-4-(4-methoxy-phenyl)-4-oxo-but-2-enoic acid;

(E)-2-Benzo[1,3]dioxol-5-yl-4-(4-methoxy-phenyl)-3-(3-methylamino-benzyl)-4-oxo-but-2-enoic acid;

(E)-2-Benzo[1,3]dioxol-5-yl-3-[3-(2-dimethyl-amino-ethoxy)-4,5-dimethoxy-benzyl]-4-(4-methoxy-phenyl)-4-oxo-but-2-enoic acid;

(E)-2-Benzo[1,3]dioxol-5-yl-3-[3,4-dimethoxy-5-(3-morpholin-4-yl-propoxy)-benzyl]-4-(4-methoxy-phenyl)-4-oxo-but-2-enoic acid;

(E)-2-Benzo[1,3]dioxol-5-yl-3-{3,4-dimethoxy-5-[3-(4-methyl-piperazin-1-yl)-propoxy]-benzyl}-4-(4-methoxy-phenyl)-4-oxo-but-2-enoic acid;

(E)-4-(4-Amino-phenyl)-2-benzo[1,3]dioxol-5-yl-4-oxo-3-(3,4,5-trimethoxy-benzyl)but-2-enoic acid; and (E)-2-Benzo[1,3]dioxol-5-yl-4-(4-dimethyl-amino-phenyl)-4-oxo-3-(3,4,5-trimethoxy-benzyl)-but-2-enoic acid.

5. A compound selected from:

(E)-2-Benzo[1,3]dioxol-5-yl-4-(4-methoxy-phenyl)-4-oxo-3-(3,4,5-trimethoxy-benzyl)-but-2-enoic acid;

(E)-3-Benzo[1,3]dioxol-5-ylmethyl-2-(4-methoxy-phenyl)-4-oxo-4-(3,4,5-trimethoxy-phenyl)-but-2-enoic acid; and (E)-4-(4-Ethoxy-3-methyl-phenyl)-2-(7-methoxy-benzo[1,3]dioxol-5-yl)-4-oxo-3-(3,4,5-trimethoxy-benzyl)-but-2-enoic acid.

6. A pharmaceutical composition comprising a therapeutically effective amount of a compound according to claim 4 in admixture with a pharmaceutically acceptable excipient, diluent, and/or carrier.

7. A method of inhibiting elevated levels of endothelin comprising administering to a host suffering therefore a therapeutically effective amount of a composition according to claim 4 in unit dosing form.

8. A method of treating vascular diseases comprising administering to a host suffering therefrom a therapeutically effective amount of a compound according to claims 4 and 5 in unit dosage form.

9. A method of treating mild or severe congestive heart failure comprising administering to a host suffering therefrom a therapeutically effective amount of a compound according to claim 4 in unit dosage form.

10. A method of treating cerebral ischemia, cerebral infarction, or embolic stroke, comprising administering to a host suffering therefrom a therapeutically effective amount of a compound according to claim 4 in unit dosage form.

11. A method of treating cerebral vasospasm, subarachnoid hemorrhage or hemorrhagic stroke comprising administering to a host suffering therefrom a therapeutically effective amount of a compound according to claim 4 in unit dosage form.

12. A method of treating diabetes comprising administering to a host suffering therefrom a therapeutically effective amount of a compound according to claim 4 in unit dosage form.

13. A method of treating gastric ulceration and mucosal damage, ischemic bowel disease, or Chrohn's disease comprising administering to a host suffering therefrom a therapeutically effective amount of a compound according to claim 4 in unit dosage form.

14. A method of treating essential and malignant hypertension comprising administering to a host suffering therefrom a therapeutically effective amount of a compound according to claim 4 in unit dosage form.

15. A method of treating pulmonary hypertension or pulmonary hypertension after bypass surgery comprising administering to a host suffering therefrom a therapeutically effective amount of a compound according to claim 4 in unit dosage form.

16. A method of treating cancer selected from human meningiomas, malignant hemangioendothelioma, metastatic prostate cancer, and benign prostatic hyperplasia comprising administering to a host suffering therefrom a therapeutically effective amount of a compound according to claim 4 in unit dosage from.

17. A method of treating myocardial infarction or ischemia comprising administering to a host suffering therefrom a therapeutically effective amount of a compound according to claim 4 in unit dosage form.

18. A method of treating acute or chronic renal failure, renal ischemia, or radiocontrast-induced nephrotoxicity comprising administering to a host suffering therefrom a therapeutically effective amount of a compound according to claim 4 in unit dosage form.

19. A method of treating endotoxic, septic or hemorrhagic shock comprising administering to a host suffering therefrom a therapeutically effective amount of a compound according to claim 4 in unit dosage form.

20. A method of treating angina comprising administering to a host suffering therefrom a therapeutically effective amount of a compound according to claim 4 in unit dosage form.

21. A method of treating preeclampsia comprising administering to a host suffering therefrom a therapeutically effective amount of a compound according to claim 4 in unit dosage form.

22. A method of treating asthma comprising administering to a host suffering therefrom a therapeutically effective amount of a compound according to claim 4 in unit dosage form.

23. A method of treating arrhythmias comprising administering to a host suffering therefrom a therapeutically effective amount of a compound according to claim 4 in unit dosage form.

24. A method of treating benign prostatic hyperplasia comprising administering to a host suffering therefrom a therapeutically effective amount of a compound according to claim 4 in unit dosage form.

25. A method of treating glaucoma comprising administering to a host suffering therefrom a therapeutically effective amount of a compound according to claim 4 in unit dosage form.

26. A method of treating male penile erectile dysfunction comprising administering to a host suffering therefrom a therapeutically effective amount of a compound according to claim 4 in unit dosage form.

27. A method of treating acute respiratory distress syndromes (ARDS) comprising administering to a host suffering therefrom a therapeutically effective amount of a compound according to claim 4 in unit dosage form.

28. A method of treating chronic obstructive pulmonary diseases comprising administering to a host suffering therefrom a therapeutically effective amount of a compound according to claim 4 in unit dosage form.

29. A method of treating cryptogenic fibrosing alveolitis comprising administering to a host suffering therefrom a therapeutically effective amount of a compound according to claim 4 in unit dosage form.

30. A method of treating atherosclerosis comprising administering to a host suffering therefrom a therapeutically effective amount of a compound according to one of claims 4 and 5 in unit dosage form.

31. A method of treating restenosis comprising administering to a host suffering therefrom a therapeutically effective amount of a compound according to one of claims 4 and 5 in unit dosage form.

32. A method of treating Raynaud's phenomenon comprising administering to a host suffering therefrom a therapeutically effective amount of a compound according to one of claims 4 and 5 in unit dosage form.

* * * * *